United States Patent [19]

Tissler et al.

[11] Patent Number: 5,578,195
[45] Date of Patent: Nov. 26, 1996

[54] SYNTHETIC CRYSTALLINE ALUMINOSILICATE FOR THE CATALYTIC CONVERSION OF HYDROCARBONS IN PETROCHEMICAL PROCESSES

[75] Inventors: Arno Tissler; Roland Thome, both of Bonn; Karl Becker, Bad Koesen; Hans-Dieter Neubauer, Merseburg; Hans-Heino John, Halle, all of Germany

[73] Assignee: Ecolith - Zeolithe GmbH, Schwandorf, Germany

[21] Appl. No.: 422,513

[22] Filed: Apr. 13, 1995

Related U.S. Application Data

[60] Division of Ser. No. 725,809, Jul. 8, 1991, Pat. No. 5,407,654, which is a continuation-in-part of Ser. No. 549,185, Jul. 6, 1990, abandoned.

[30] Foreign Application Priority Data

Jul. 11, 1990 [DE] Germany ................. 40 22 140.7

[51] Int. Cl.[6] ................. C10G 11/05; C07C 4/06; C07C 5/22
[52] U.S. Cl. ................. 208/46; 208/120; 585/407; 585/418; 585/467; 585/481; 585/640; 585/739
[58] Field of Search ................. 208/46, 120; 585/407, 585/418, 467, 640, 481, 739

[56] References Cited

U.S. PATENT DOCUMENTS

| | | | |
|---|---|---|---|
| 3,702,886 | 11/1972 | Argauer et al. | 423/328 |
| 3,758,403 | 9/1973 | Rosinski et al. | 208/120 |
| 4,175,114 | 11/1979 | Plank et al. | 423/329 |
| 4,199,556 | 4/1980 | Plank et al. | 423/329 |
| 4,257,885 | 3/1981 | Grose et al. | 210/691 |
| 4,341,748 | 7/1982 | Plank et al. | 423/328 |
| 4,415,544 | 11/1993 | Kokotailo et al. | 423/328 |
| 4,533,533 | 8/1985 | Dewing et al. | 423/328 |
| 4,562,055 | 12/1985 | Arika et al. | 423/329 |
| 4,654,316 | 3/1987 | Barri et al. | 502/61 |
| 4,687,654 | 8/1987 | Taramasso et al. | 423/329 |
| 4,818,509 | 4/1989 | Dwyer et al. | 423/329 |
| 4,825,444 | 4/1989 | Johna et al. | 372/41 |
| 4,891,199 | 1/1990 | Latourette et al. | 423/328 |
| 4,900,529 | 2/1990 | Sanchez et al. | 423/328 |
| 4,954,326 | 9/1990 | Onodeon et al. | 423/328 |
| 4,994,251 | 2/1991 | Plank et al. | 423/328 |
| 5,102,644 | 4/1992 | Plank et al. | 423/328 |
| 5,190,902 | 3/1993 | Demmel | 502/63 |
| 5,258,566 | 11/1993 | Kresge et al. | 585/467 |
| 5,349,114 | 9/1994 | Lago et al. | 585/418 |
| 5,385,714 | 1/1995 | Thome et al. | 502/64 |
| 5,396,009 | 3/1995 | Verduijn | 585/418 |
| 5,407,654 | 4/1995 | Tissler et al. | 502/64 |
| 5,421,992 | 6/1995 | Zones et al. | 585/481 |

FOREIGN PATENT DOCUMENTS

| | | |
|---|---|---|
| 8821025 | 3/1989 | Australia. |
| 21674 | 1/1981 | European Pat. Off. |
| 21675 | 1/1981 | European Pat. Off. |
| 26963 | 4/1981 | European Pat. Off. |
| 40104 | 11/1981 | European Pat. Off. |
| 87720 | 9/1983 | European Pat. Off. |
| 104006 | 4/1984 | European Pat. Off. |
| 0138680 | 4/1985 | European Pat. Off. |
| 0150256A3 | 8/1985 | European Pat. Off. |
| 0044631B1 | 12/1985 | European Pat. Off. |
| 0170751 | 2/1986 | European Pat. Off. |
| 0306238A2 | 3/1989 | European Pat. Off. |
| 0406474A2 | 1/1991 | European Pat. Off. |
| 207186 | 2/1984 | Germany. |
| 3922181A1 | 1/1991 | Germany. |
| 206551 | 2/1994 | Germany. |
| 57-007819 | 1/1982 | Japan. |
| 58-04511 | 3/1983 | Japan. |
| 59-039716 | 3/1984 | Japan. |
| 63-0227277 | 9/1988 | Japan. |

OTHER PUBLICATIONS

R. Szostak, "*Molecular Sieves Principles of Synthesis and Identification*", Van Nostrand Reinhold, p. 368, 384 (1989).
Peter A. Jacobs et al., "*Synthesis of High–Silica Aluminosilicate Zeolites*", Studies in Surface Science and Catalysis vol. 33, pp. 113–146 (1987).
R. Szostak, "*Molecular Sieves Principles of Synthesis and Identification*", Van Nostrandi Reinhold, pp. 283–347.
W. Schwieger et al., "*Synthesis of Pentasil Zeolites With and Without Organic Templates*", American Chemical Society, Chpt. 20 (1989).
Feng–Yuen Dai et al., "*Crystallization of Pentasil Zeolite in the Absence of Organic Templates*", American Chemical Society, Chpt. 18, (1989).
N. R. Meshram Zeolites, 6, pp. 434–438 (1986).

Primary Examiner—Anthony McFarlane
Attorney, Agent, or Firm—Darby & Darby, P.C.

[57] ABSTRACT

Synthetic crystalline aluminosilicate of the pentasil type and method for using the same as catalysts or catalyst components in petrochemical processes for the catalytic conversion of hydrocarbons and their derivatives into useful organic compounds and intermediates.

22 Claims, 5 Drawing Sheets

SILICON

ALUMINUM

ALUMINUM
SILICON

ALUMINUM
SILICON

SYNTHETIC CRYSTALLINE ALUMINOSILICATE FOR THE CATALYTIC CONVERSION OF HYDROCARBONS IN PETROCHEMICAL PROCESSES

This is a division of application Ser. No. 07/725,809, filed Jul. 8, 1991, now U.S. Pat. No. 5,407,654, which is a continuation-in-part of U.S. patent application Ser. No. 549,185, filed Jul. 6, 1990, now abandoned, the disclosure of which is incorporated herein by reference in its entirety.

The present invention relates to synthetic crystalline aluminosilicates and their use as catalysts or catalyst components in petrochemical processes for the conversion of hydrocarbons and their derivatives into valuable organic intermediates. The chemical composition of the aluminosilicates of the invention is described in terms of molar ratios in the following manner:

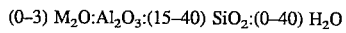

$(0-3)\ M_2O:Al_2O_3:(15-40)\ SiO_2:(0-40)\ H_2O$ wherein M represents an alkali metal cation, proton, or an ammonium compound.

BACKGROUND OF THE INVENTION

The development and application of molecular sieve catalysts with shape-selective properties has, without doubt, provided an impetus in recent decades to the development of crude oil processing and petrochemistry. This is so particularly since the discovery of silicon-rich zeolites of medium pore size of the pentasil type.

Pentasil aluminosilicate zeolites are important catalysts in the petroleum and chemical industries and have been applied in processes which (1) lower or eliminate lead and benzene in motor gasoline; (2) replace concentrated liquid or carrier-supported mineral acid catalysts, i.e. sulfuric acid, hydrofluoric acid and phosphoric acid, in aromatic alkylation and olefin hydration processes; and (3) limit the content of aromatics and sulfur in diesel fuels.

Structurally, pentasil zeolites are characterized by an intracrystalline system of mutually crossing channels with a diameter of about 5.5 angstroms. The crossing regions have a very weakly pronounced cage character and are frequently the site of the reaction occurrence. In addition to the acid strength of the acidic centers and their concentration, pore shape and size have an important influence on the activity and selectivity of the conversion of materials and material mixtures.

The size of the pore canals permits the entry and exit of linear and once branched aliphatic molecules and of aromatic molecules with a single benzene ring with up to 10 carbon atoms. Molecules of this class are converted chemically within the pore structure and released as product by diffusion processes. The intracrystalline diffusion rate varies considerably between members of this class due to the differences in molecular size and form. In cases where the activated state of the molecule requires more space than can be satisfied by the crossing regions of the pentasil zeolites, such reactions do not proceed or proceed only with very low probability. This selective property in zeolites is known as shape-selectivity.

The behavior of zeolite catalysts is largely determined by fine differences within the aluminosilicate structure. For example, it is known that the aluminum distribution over the cross section of pentasil zeolite crystals synthesized using organic template compounds is different from that of pentasil zeolite crystals obtained from strictly inorganic synthesis batches (see, for example, A. Tissler et al. *Stud. Surf. Sci. Catal.* Vol. 46, pages 399–408 (1988)). For the former case, aluminum accumulation in the periphery of the crystals is observed; for the latter, the aluminum over the cross section of the crystals predominates. Structural information of the zeolite provided by X-ray crystal diffraction is therefore not sufficient to characterize the catalytic utility of such materials and needs to be supplemented by more subtle methods such as solid state high resolution nuclear magnetic resonance (NMR) spectroscopy. For a review on the applications of solid state NMR in structural characterization of zeolites, see, Engelhardt, G. et al. "High-Resolution Solid State NMR of Silicates and Zeolites," Wiley; Chichester, England, 1987.

Pentasil zeolites in their protonated form catalyze a variety of reaction types which include: (1) dehydration/hydration (ethers and alkenes from alcohols, alcohols from alkenes), (2) carbon-carbon bond linking reactions (oligomerization of alkenes, condensations of oxygen-containing compounds and alkylation of aromatic compounds and isoparaffins); (3) carbon-carbon bond splitting reactions (cracking processes of paraffins and alkenes); (4) aromatization (synthesis of aromatic compounds from paraffins and alkenes); and (5) isomerizations (backbone and double bond isomerizations).

Methods for the synthesis of aluminosilicates are described extensively in the technical and patent literature (see, for example, Jacobs, P. A. et al. (1987) *Stud. Surf. Sci. Cat.*, Vol. 33, pages 113–146). The reported methods for the synthesis of aluminosilicates, however, suffer from a variety of serious disadvantages which preclude their use for industrial scale, non-polluting production. Examples of such disadvantages include: (1) the use of materials which are toxic and inflammable; (2) formation of undesirable secondary phases, e.g. quartz, in the zeolite product; (3) prolonged reaction times; (4) incomplete reactions; and (5) the use of high temperatures to remove organic contaminants, e.g. structure-directing compounds as quaternary ammonium salts, present in the zeolite lattice which damages the lattice structures leading to a reduction in the catalytic properties. In addition, formation of toxic effluents under conventional synthetic hydrothermal conditions necessitates costly pollution control equipment.

For example, U.S. Pat. No. 3,702,886 discloses the synthesis of silicon-rich zeolites of the pentasil family. The disclosed methods for zeolite synthesis requires the presence of organic, structure-directing compounds or templates in the reaction mixture. Tetralkylammonium compounds, e.g. tetrapropylammonium bromide, are generally used for this purpose.

U.S. Pat. No. 4,257,885 discloses a process for preparing zeolites which omits the use of organic templates. The synthetic processes described therein lead to the desired product under prolonged (several days) reaction times which may not reach completion.

Accordingly, there is a substantial need in the field for improved methods for preparing crystalline aluminosilicates which avoid at one or more of the deficiencies mentioned above. Furthermore, there is an acute need in the art for synthetic, crystalline aluminosilicates which display enhanced catalytic properties, long-term stability, and higher selectivity over conventional aluminosilicates in petrochemical processes.

SUMMARY OF THE INVENTION

The present invention relates to synthetic crystalline aluminosilicates and methods for using the same as catalysts or components in heterogeneous catalysts for petrochemical processes for the conversion of hydrocarbons and their derivatives into valuable organic intermediates.

The synthetic crystalline aluminosilicates are produced by hydrothermal crystallization from an inorganic aqueous alkaline reaction mixture having a composition of $SiO_2/Al_2O_3$ at a molar ratio between about 15 and about 40; $OH^-/SiO_2$ at a molar ratio between about 0.1 to about 0.2; and a $H_2O/SiO_2$ at a molar ratio between about 20 and about 60.

The aluminosilicates of the present invention display enhanced catalytic properties, long-term stability, and higher selectivity over conventional aluminosilicates. In addition, the inventive aluminosilicates are synthesized by a strictly inorganic method which excludes formation of undesirable secondary phases, prolonged reaction time, and produces higher product yield over conventional methods. In addition, the inventive aluminosilicates have a low coking tendency which allows long operating periods between catalyst regeneration.

The inventive aluminosilicate can be used as catalysts and catalyst components for converting hydrocarbons and its derivatives into valuable intermediates in the petrochemical industries. For example, the aluminosilicates can be used in processes for (1) removing n-paraffins or once branched paraffins from hydrocarbon fractions; (2) processing of mixtures of C8 aromatic compounds; (3) alkylating aromatic compounds with low molecular weight alkenes and alcohols; (4) cracking higher-boiling hydrocarbon fractions on agitated catalysts; (5) isomerizing low molecular weight n-paraffins to iso-paraffins; (6) generating aromatic compounds from low molecular weight hydrocarbons; (7) generating liquid hydrocarbons from low molecular weight alkanes and alkenes and (8) converting alcohols to hydrocarbons, low molecular weight alkenes and aromatic compounds.

OBJECTS OF THE INVENTION

Accordingly, it is an object of the invention to provide a synthetic, crystalline aluminosilicate of the pentasil type having a largely homogeneous distribution of aluminum over the crystalline cross-section, hence a surface molar ratio of $SiO_2:Al_2O_3$ which is equal to or greater than the interior molar ratio of $SiO_2:Al_2O_3$ in the crystal. The aluminosilicate of the present invention exhibits enhanced catalytic properties, selectivity, and stability over known aluminosilicates prepared by conventional methods employing organic templates.

It is another object of the invention to provide a method of using the inventive aluminosilicate as a catalyst or a component of a heterogenous catalyst for the catalytic conversion of hydrocarbons and their derivatives in petrochemical processes.

It is yet another object of the invention to provide a practical method for preparing synthetic crystalline aluminosilicates which does not require the use of organic templates and prolonged reaction times, does not produce undesirable secondary phases and produces a higher product yield over conventional methods.

These and other objects of the invention will be apparent in light of the detailed description below.

DETAILED DESCRIPTION OF THE INVENTION

Figure 1:
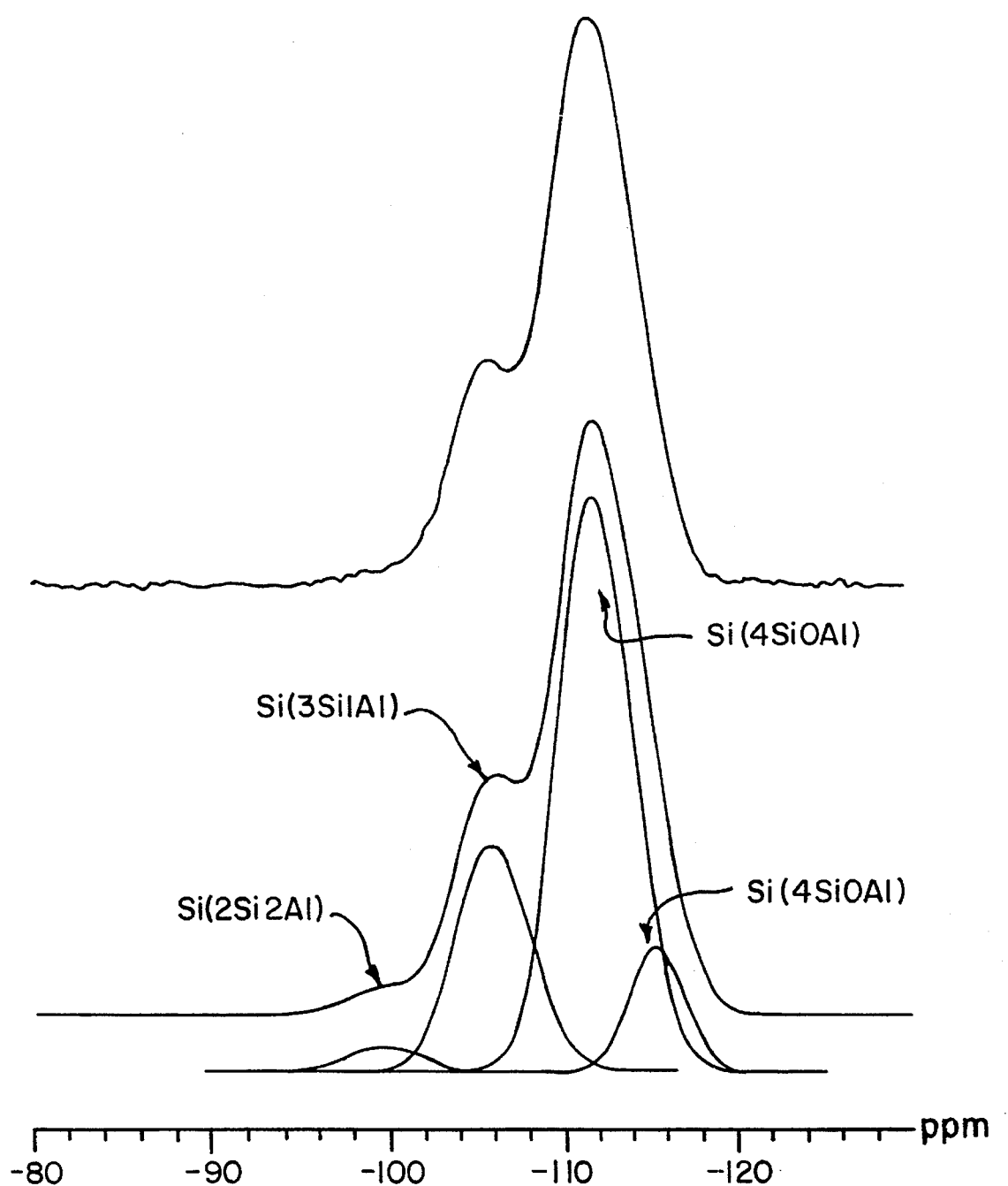
FIG. 1 is a $^{29}Si$ solid state MAS NMR spectrum of the aluminosilicate type A zeolite prepared in accordance with Example 1.

All literature references, patents and patent applications cited in this specification are hereby incorporated by reference in their entirety.

The present invention relates to a synthetic, crystalline aluminosilicate and a method for using the same as catalyst components in petrochemical processes for the conversion of hydrocarbons and their derivatives into valuable organic compounds.

The chemical composition of the synthetic crystalline aluminosilicates of the invention is described in terms of molar ratios in the following manner:

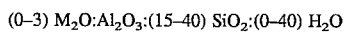

$(0-3)\ M_2O:Al_2O_3:(15-40)\ SiO_2:(0-40)\ H_2O$ wherein M represents an alkali metal cation such as sodium, potassium, or lithium, preferably sodium; a proton or an ammonium compound.

The synthetic crystalline aluminosilicates are produced by hydrothermal crystallization from an inorganic aqueous alkaline reaction mixture containing silicon dioxide and aluminum oxide or their hydrated derivatives or alkali silicates and aluminates and mineral acid. Preferably, relatively inexpensive starting materials of sodium water glass (sodium silicate) and sulfuric acid as mineral acid are used.

The reaction mixture contains $SiO_2/Al_2O_3$ at a molar ratio of between about 15 and about 40, preferably between about 20 to about 30; $OH^-/SiO_2$ at a molar ratio between about 0.1 to about 0.2, preferably between about 0.13 to about 0.16; and $H_2O/SiO_2$ at a molar ratio between about 20 and about 60, preferably between about 30 to about 40.

The reaction mixture, contained in a stirred autoclave, is subjected to hydrothermal crystallization conditions. In general, the reaction is conducted at a constant temperature between about 100° C. to 325° C., preferably between about 180° C. to about 250° C. for a time period of about 1 to about 100 hours, preferably about 24 hours during which the crystalline product precipitates out.

The aluminosilicates of the present invention can be crystallized in a single step at a constant temperature and within a predetermined time period or in a series of steps. For example, the mixture can be maintained at different constant temperatures for various time periods, or at a plurality of different temperatures for a different time period at each temperature but only within the aforementioned time and temperature ranges.

Optionally, partially or totally crystalline aluminosilicate seed material can be added to the reaction mixture to increase the crystallization rate. The amount of seeding material that can be added is generally about 1 to about 10%, preferably about 1 to about 3% by weight of the total mixture.

The crystalline aluminosilicate is then separated from the mixture by conventional means, e.g. filtration, and throughly washed with water to remove adhering impurities. The aluminosilicate is then dried at about 150° C. for about 7 hours. The general yield of aluminosilicate crystals recovered is about 80 to about 99%, usually 95%.

In general, the crystalline aluminosilicates have a particle size between about 0.1 to about 10 μm, usually about 3 μm. The pore size of the inventive aluminosilicates, as determined by XRD structure analysis, generally range between about 5.4 and about 5.7 angstroms, usually about 5.5 angstroms. The surface area of the aluminosilicate of the present invention is generally greater than 300 m$^2$/gm as determined by the conventional BET method.

Thereafter, the inventive aluminosilicate is then subjected to an ion exchange process with an ammonium compound or a mineral acid to ultimately produce effective, heterogeneous acidic catalysts. Methods for carrying out ion exchange reactions of zeolites are well known in the art and are described, for example, in Jacobs, P. A. et al. (1987) *Stud. Surf. Sci. Cat.* Vol. 33.

Non-limiting examples of suitable mineral acids for use in the exchange process include sulfuric acid, hydrochloric acid, and nitric acid. Preferred mineral acids are sulfuric acid and hydrochloric acid.

Suitable, but non-limiting examples, of ammonium compounds include ammonium sulphate, ammonium nitrate, ammonium chloride, and ammonium acetate. Preferred ammonium compounds for use in the present invention are ammonium sulphate and ammonium chloride. The concentration of ammonium compound in solution is broadly between about 0.1 and about 5N, preferably about 1N.

The aluminosilicate treated by an ion exchange process is then converted by a subsequent calcination into an active hydrogen form at a temperature above 300° C., preferably between about 400° and about 600° C.

The active hydrogen form of the aluminosilicate can be transformed into finished catalysts by the addition of inorganic or organic binders and optionally metal or metal oxide components.

Non-limiting examples of inorganic binders suitable for use with the inventive aluminosilicate are amorphous silica, pseudo-boehmite, kaolin, and other clays or a combination of the foregoing. Optional organic binders or auxiliaries, such as polyvinyl alcohol, may be added. Preferred binders for use in this invention are amorphous silica and kaolin. The aluminosilicates can also be mixed with a variety of commercial catalysts, e.g. octane enhancing fluid catalystic cracking (FCC) additives.

Suitable examples of metal components which can be used with the inventive aluminosilicate include elements of the 4th and 6th period of the periodic table. Preferred metals are Zn, Mo, W, Pd, Ga, Pt or combinations thereof.

Non-limiting examples of metal oxide components include gallium oxide, molybdenum oxide, nickel-oxide, platinum oxide, and palladium oxide. Preferred metal oxides for use are gallium-oxide, molybdenum oxide and nickel-oxide.

Figure 4:
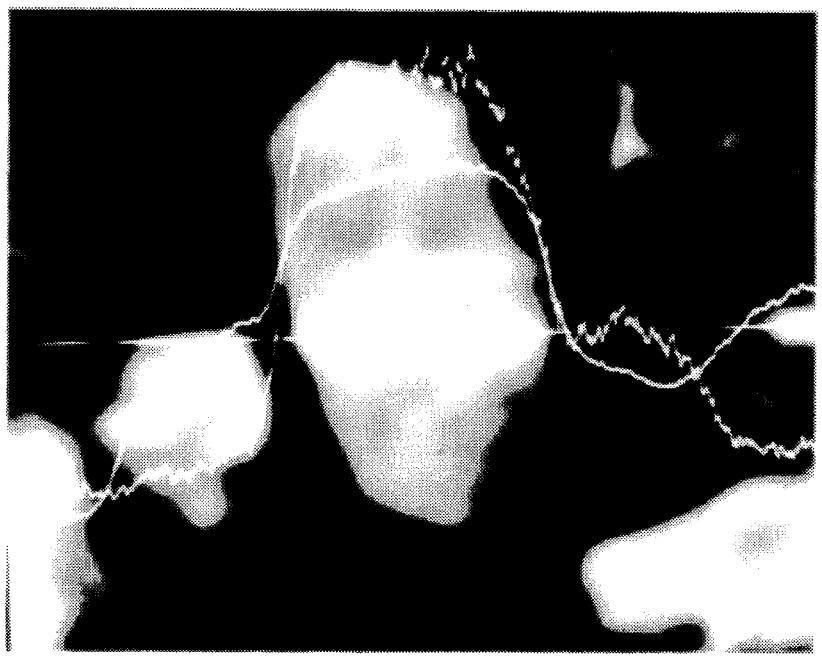
FIG. 4 is an electron beam micro-probe analysis illustrating the cross-sectional aluminum distribution of aluminumsilicate type A zeolite prepared in accordance with Example 1.
Figure 5:
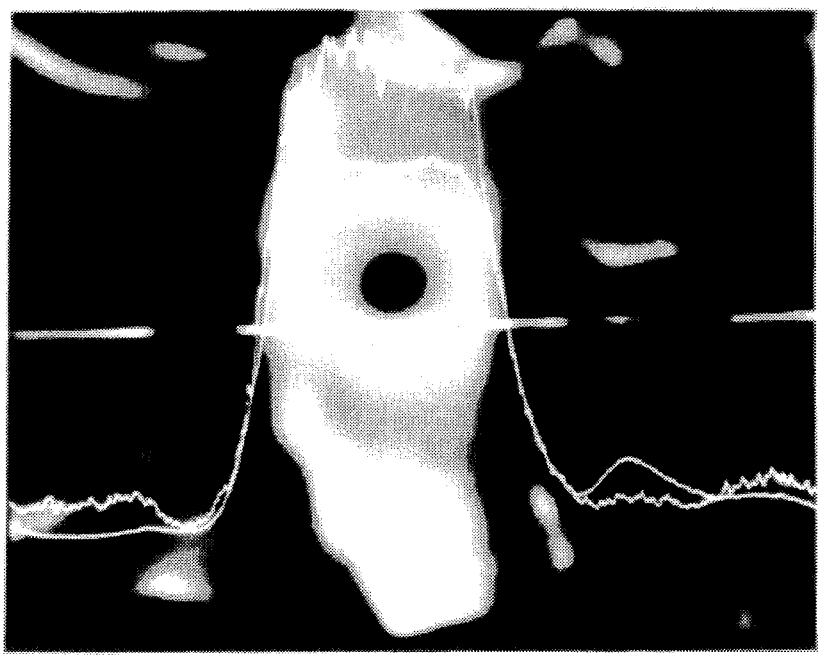
FIG. 5 is an electron beam micro-probe analysis illustrating the cross-sectional aluminum distribution of aluminumsilicate type B zeolite prepared in accordance with Example 2.
Figure 6:
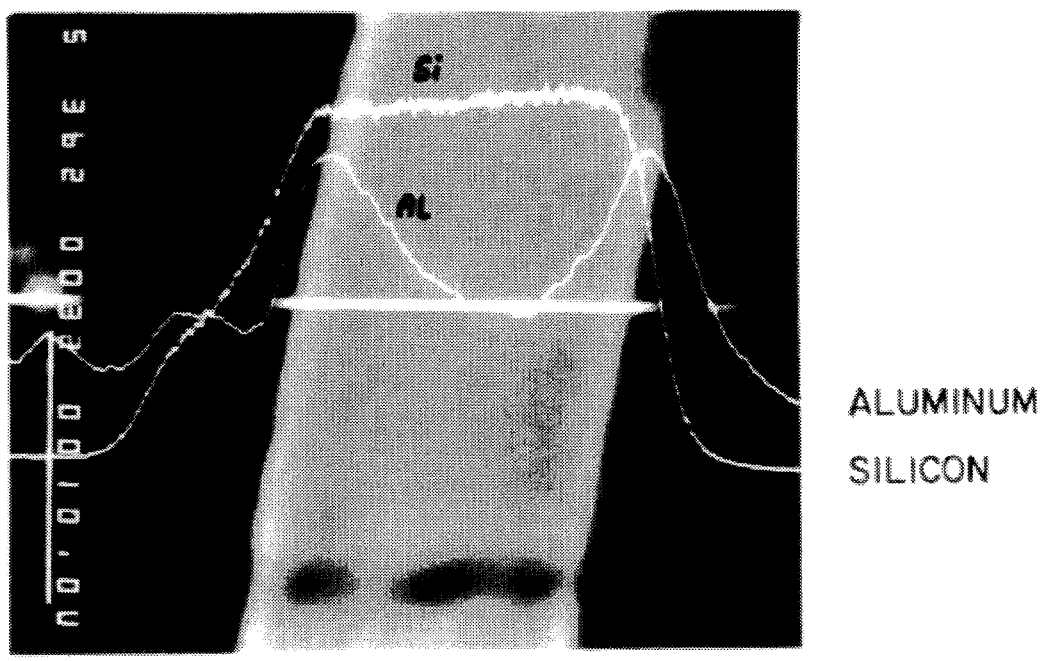
FIG. 6 is an electron beam micro-probe analysis illustrating the cross-sectional aluminum distribution of a conventional aluminosilicate type C zeolite prepared in accordance with Example 3. This figure demonstrates the accumulation of aluminum at the periphery of the zeolite crystals.

The inventive aluminosilicates have a largely homogeneous distribution of aluminum over the cross section of the crystals as shown in FIGS. 4 and 5. By comparison, FIG. 6 shows the accumulation of aluminum at the crystalline edge of an aluminosilicate prepared by a conventional method in the art.

The elementary distributions of silicon and aluminum over the cross-section of the aluminosilicate of the A, B and C-type (FIGS. 4 to 6) were determined by means of an electron beam micro-probe IEOL 1XA-733 with a DEC-computer PDP 11/23. Samples were embedded into resin, polished with diamond paste and sputtered with gold. The electron beam measurements were conducted with a voltage of 15 kV and a correct intensity of 50 μA. The elementary distributions of aluminosilicate types A, B, C were obtained by electron beam deflection and the resultant scanning electron micrographs of the crystals were recorded on photopaper.

The aluminosilicates of the invention have a surface molar ratio of $SiO_2:Al_2O_3$ which is equal to or greater than the interior molar ratio of $SiO_2:Al_2O_3$. The ratio of surface molar ratio of $SiO_2:Al_2O_3$ to the interior molar ratio of $SiO_2:Al_2O_3$ in the aluminosilicates of the invention is broadly between about 1:1 and about 1.5:1, preferably between about 1:1 and about 1.1:1.

The inventive aluminosilicates can be physically distinguished from conventional aluminosilicates by means of X-ray crystal diffraction patterns and by solid state NMR spectroscopy. For example, the X-ray diffraction diagrams of the inventive aluminosilicate contain at least the distances between the crystalline lattice shown in Table 1.

Figure 2:
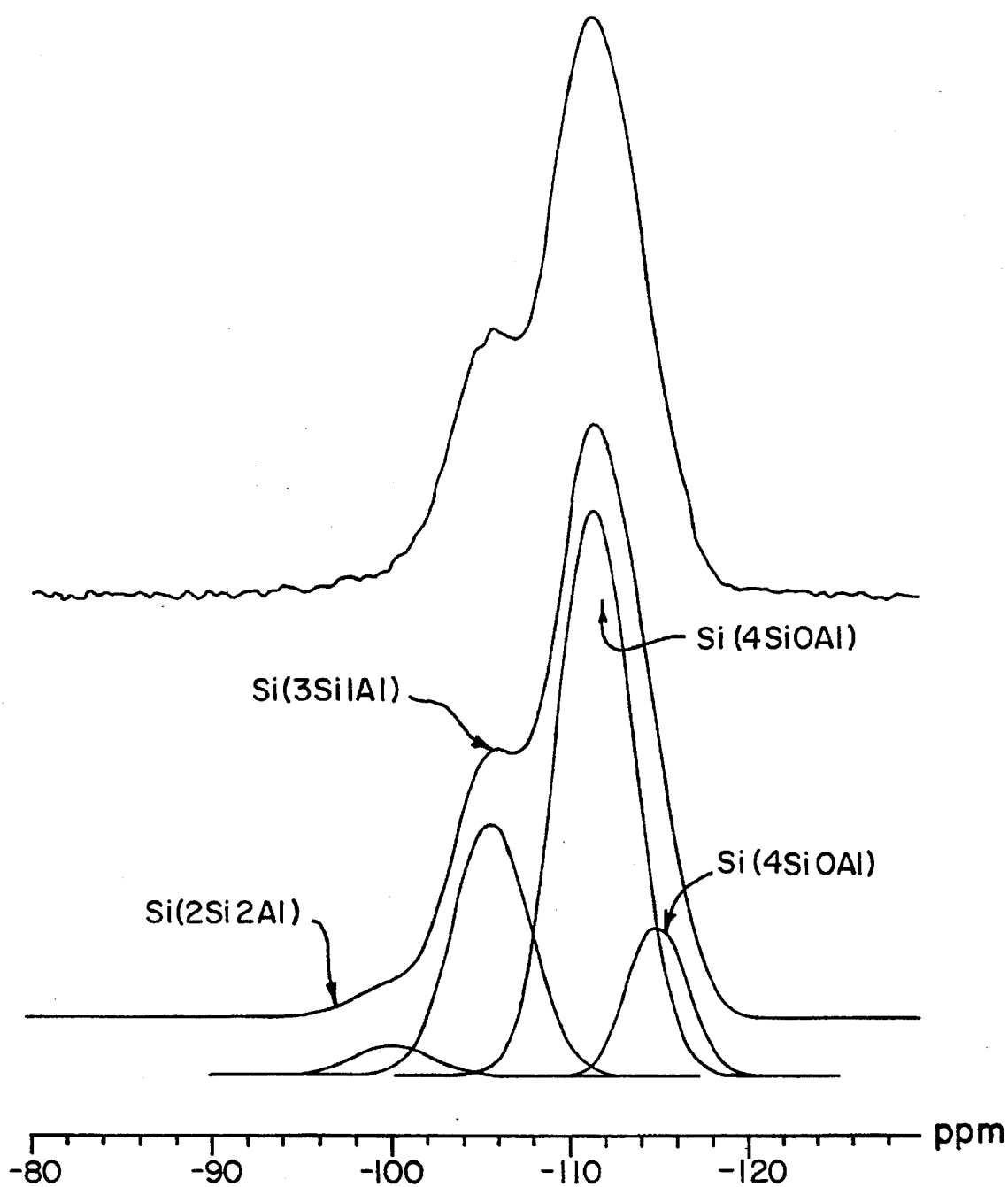
FIG. 2 is a $^{29}Si$ solid state MAS NMR spectrum of aluminosilicate type B zeolite prepared in accordance with Example 2.
Figure 3:
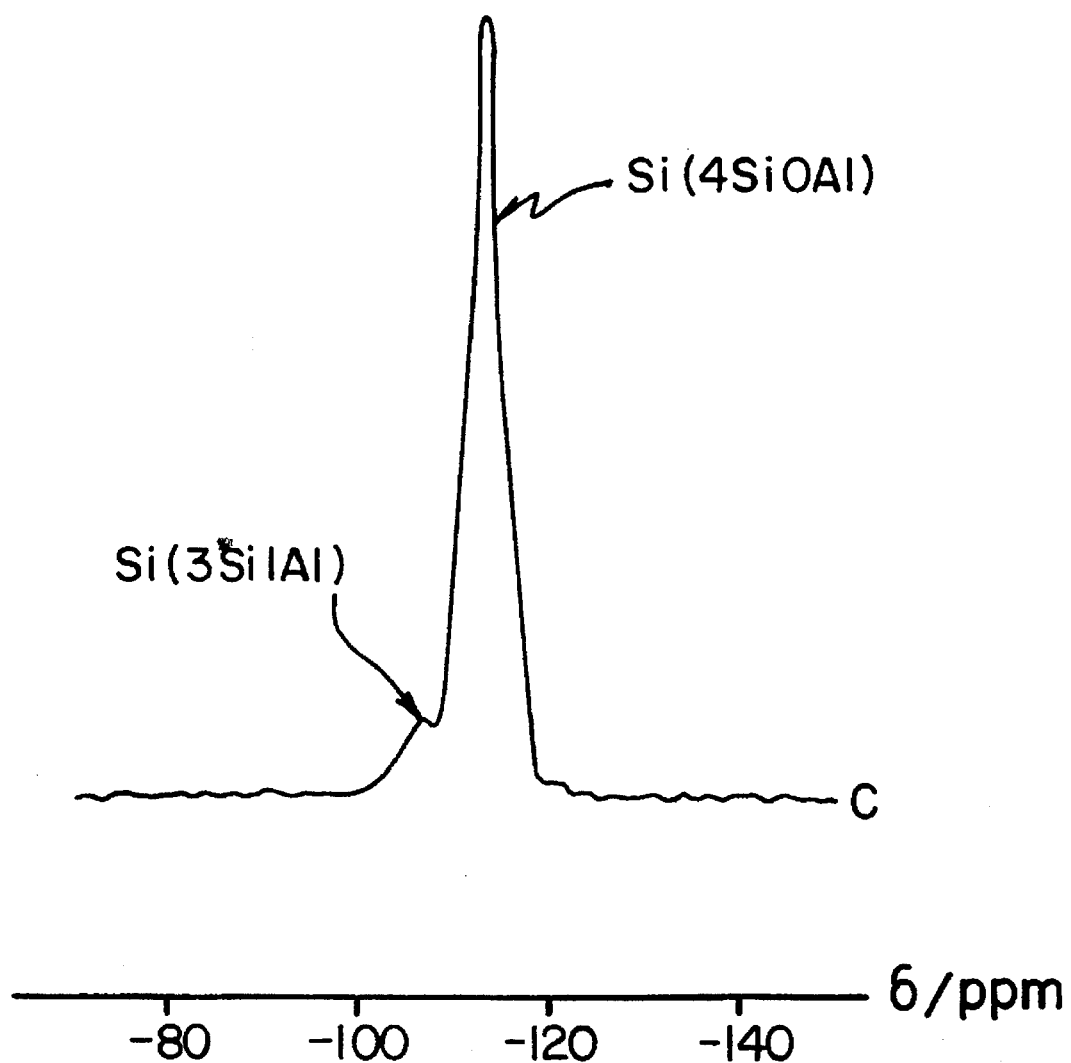
FIG. 3 is a $^{29}Si$ solid state MAS NMR spectrum of aluminosilicate type C zeolite prepared in accordance with Example 3.

The aluminosilicates prepared by the method of the present invention produce a $^{29}Si$ solid state Magic Angle Spin (MAS) NMR spectrum with characteristic absorption bands at −100, −106, −112, and −116 ppm relative to the adsorption band of tetramethylsilane. The high-resolution solid-state NMR spectra shown in FIGS. 1 to 3 were performed with a Bruker 400 MSL spectrometer with a magnetic field of 9.4 T. The $^{29}Si$ high-resolution NMR measurements were conducted at a frequency of 79.5 MHz with a pulse length of 4 microseconds, a pulse interval of 5 seconds, an spin rpm of 3 KHz with a total of 10,000 scan aquisitions. The Bruker GLINFIT program was used for simulating the individual peaks in the measured spectrum.

The inventive aluminosilicate can be used as a catalyst or a component of heterogenous catalysts in petrochemical processes for the catalytic conversion of hydrocarbons or their derivatives.

In processes where the aluminosilicate is employed, the operational pressures are generally between about 0.1 and about 15 MPa, preferably between about 1 and about 10 MPa; the temperatures are generally between about 250° and about 600° C., preferably between about 300° and about 500° C.; and with raw material loads between about 0.5 and about 10 (v/v/hour), preferably between about 2 and about 8 (v/v/hour). Such processes can be conducted in the presence of hydrogen gas or hydrogen-containing gases in molded catalysts containing the inventive aluminosilicate.

In one embodiment of the invention, the aluminosilicates can be employed in processes for dewaxing or removing paraffins from hydrocarbon fractions. Long-chain linear or slightly branched paraffins have higher melting points than do other hydrocarbons with the same number of carbon atoms. Small amounts of such wax-like components in mixtures, e.g. fuel distillates and lubricating oils, can negatively affect the flow behavior (pour point, freezing point, cloud point).

Unlike narrow pore zeolites, e.g. erionite, having shape-selective cracking properties restricted to gasolines, the medium pore aluminosilicates are especially suitable for selectively cracking paraffins and removing them from mixtures such as jet fuel and distillation residues. Example 5 illustrates the utility of the inventive aluminosilicates in dewaxing hydrocarbon fractions.

In another embodiment of the invention, the aluminosilicates of the present invention are used in processes for the isomerization of xylene. In general, the starting materials for xylene isomerization are mixtures of $C_8$ aromatic compounds consisting of ethyl benzene as well as ortho-, meta- and paraxylene. Para- and ortho-xylenes are important intermediates for the production of plastics.

In xylene isomerization processes, two goals must be met (1) to achieve an equilibrating isomer population of 50% m-xylene and 25% each of ortho- and para-xylene after a large portion of para-xylene has been removed and (2) to convert ethylbenzene into xylenes. For optimization of the isomerization process, it is important that the zeolite catalyzes isomer equilibration under conditions which maximal ethylbenzene conversion occurs. Example 6 illustrates the utility of the inventive aluminosilicate in xylene isomerization.

In yet another embodiment of the invention, the inventive aluminosilicate is used in processes for the alkylation of aromatic compounds with low molecular weight alkenes and alcohols. Aluminosilicates have proven useful in processes for preparing xylene from toluene; methanol and ethylbenzene from benzene and ethene; para-ethyltoluene from toluene and ethyl ether or ethanol; diethylbenzene from ethylbenzene and ethene; dimethylbenzene from xylene and ethene; cumene from benzene and propene; alkylbenzene from benzene and low molecular weight alcohols; and diethylbenzene from ethylbenzene and ethanol. Example 7 illustrates the utility of the inventive aluminosilicates in the alkylation of benzene and ethylbenzene with ethene. In addition, Example 8 illustrates the use of the inventive aluminosilicates in the alkylation of toluene with methanol.

In another embodiment of the invention, the aluminosilicates are used in catalytic, fluidized bed cracking processes for the conversion of vacuum distillates and distillation residues into high-grade fuels with high research octane numbers/motor octane numbers. For this purpose, catalysts, such as FCC catalysts, which incorporate aluminosilicate zeolites in its matrix are generally employed. Examples of FCC catalysts include Y-zeolites and rare earth exchanged y-zeolites. The addition of pentasil zeolites in the finished catalyst brings about the elimination of low-octane paraffin fractions and the formation of $C_3$ and $C_4$ olefins which are useful starting material for alkylation reactions. Example 9 illustrates the use of the inventive aluminosilicates in a process for cracking high-boiling hydrocarbon fractions. In addition, Example 10 details the use of the inventive aluminosilicates in a process for isomerizing low molecular weight n-paraffins to improve the front octane number.

In a further embodiment of the invention, the aluminosilicates are used in processes for obtaining aromatic compounds from low molecular weight hydrocarbons. Traditionally, aromatics from crude oil are produced by a gas reforming process. This process, however, is able to aromatize only hydrocarbons having at least six carbon atoms. In recent years, utilization of light hydrocarbon fractions ($C_2$ to $C_5$) particularly in liquified form has become more important for obtaining high-grade liquid products. Conventional aromatizing catalysts which catalyze the dehydrocyclodimerization of light fractions also form coke which deactivates the catalyst during prolonged operations. Accordingly, shape-selective zeolites with low coking tendencies would be particularly suitable in such processes. Example 11 describes the use of the inventive aluminosilicates in a process for generating aromatic compounds from low molecular weight hydrocarbons.

In a still further embodiment of the invention, the synthetic aluminates are used in processes for obtaining liquid hydrocarbons or low molecular weight alkenes from methanol. Methanol derived from known processes from natural gas or coal is an important intermediate for the production of high-grade hydrocarbons. Pentasil zeolites have shown utility in catalytic processes for the conversion of methanol into higher molecular weight hydrocarbons such as high-grade gasoline for carburetor-type gasoline engines, aromatic compounds as intermediates for the plastics industry and alkenes. Example 12 describes in detail the utility of the inventive aluminosilicates in a process for obtaining liquid hydrocarbons or low molecular weight alkenes from methanol.

The following examples illustrate the invention without limiting its scope.

Example 1

Synthesis of an Aluminosilicate of Type A

A 25,000 liter reaction solution containing sodium water glass, aluminum sulfate, sodium sulfate and sulfuric acid in the molar ratios of: $SiO_2/Al_2O_3=30$; $OH^-/SiO_2=0.14$; $H_2O/SiO_2=30$ is heated in a stirred 35,000 liter autoclave to a reaction temperature of 185° C. and pressure of 10 bar for 24 hours. The solid product (>90% yield) is filtered off and dried at 110° C. The dry substances consist of a pure-phase alumino-silicate with an X-ray diffraction diagram with at least the d values (angstroms) that are listed in Table 1 below. The peak-plane intensities are relative to the strongest peak which is set at 100%.

TABLE 1

| d Value/Interlattice Plane Distance (in angstroms) | Relative Intensity |
|---|---|
| 11.2 ± 0.3 | strong |
| 10.2 ± 0.3 | strong |
| 9.8 ± 0.2 | weak |
| 3.85 ± 0.1 | very strong |
| 3.83 ± 0.1 | strong |
| 3.75 ± 0.1 | strong |
| 3.73 ± 0.1 | strong |
| 3.60 ± 0.1 | weak |
| 3.60 ± 0.05 | weak |
| 3.00 ± 0.05 | weak |
| 2.01 ± 0.02 | weak |
| 1.99 ± 0.02 | weak |

The chemical composition of the product, expressed in molar ratios, is: $1.1Na_2O:Al_2O_3:31SiO_2:6H_2O$. FIG. 4 shows the aluminum distribution over the cross section of the crystals of the products.

The proportions of the individual absorption bands, which were obtained from the $^{29}Si$ solid state MAS nuclear magnetic spectra (FIG. 1) and are a measure of the different tetrahedral coordination of silicon, occur at:

| Si(4SiOAl) % −112 and −116 ppm | Si(3Si1Al) −106 ppm | Si(2Si2Al) −100 ppm |
| --- | --- | --- |
| 75 | 23 | 2 |

EXAMPLE 2

Synthesis of an Aluminosilicate of Type B

In accordance with Example 1, a reaction formulation of a solution of sodium water glass, aluminum sulfate, sodium sulfate and sulfuric acid in the molar ratios of: $SiO_2/Al_2O_3=$ 24; $OH^-/SiO_2=0.14$; $H_2O/SiO_2=30$ is heated in stirred autoclave to a reaction temperature of 185° C. and treated hydrothermally for 24 hours. The solid product is filtered off and dried at 110° C. The dry substance consists of a pure-phase aluminosilicate with an X-ray diffraction diagram with at least the d values that are listed in Table 1 shown in Example 1.

The chemical composition of the product, expressed in molar ratios, is: $1.1Na_2O:Al_2O_3:23SiO_2:7H_2O$. FIG. 5 shows the aluminum distribution over the cross section of the crystals of the products.

The proportions of the individual absorption bands, which were obtained from the $^{29}Si$ solid state MAS nuclear magnetic spectrum (FIG. 2) and are a measure of the different tetrahedral coordination of silicon, occur at:

| Si(4SiOAl) % −112 and −116 ppm | Si(3Si1Al) −106 ppm | Si(2Si2Al) −100 ppm |
| --- | --- | --- |
| 71 | 26 | 3 |

EXAMPLE 3

Preparation of a Conventional Comparison Aluminum Silicate of Type C

A reaction formulation of pyrogenic silica, tetrapropylammonium bromide, glycerol, ammonia, sodium hydroxide, aluminum nitrate and with the molar ratios of: $SiO_2/Al_2O_3=72$; $Na_2O/SiO_2=0.2$; $TPA/SiO_2=1.25$; $glycerol/SiO_2=19.86$; $NH_3/SiO_2=0.2$; $H_2O/SiO_2=146$ is heated in a stationary autoclave to a reaction temperature of 150° C. and treated hydrothermally for 72 hours. The reaction components and conditions are described in (1987) Jacobs, P. A. et al. Stud. Surf. Sci. Catal. Vol. 33. The solid product is filtered off and dried at 110° C. The product has a $SiO_2/Al_2O_3$ ratio of 70.

The aluminum distribution of the cross section of crystals of the conventional comparison silicate is shown in FIG. 6. Moreover, this product does not show any absorption bands in the 29-silicon solid MAS nuclear resonance spectrum at −100 ppm (see FIG. 3).

EXAMPLE 4

The Preparation of Catalysts from crystalline Aluminosilicate

Catalyst 1

A synthetic, crystalline aluminosilicate of type B prepared in accordance with Example 2 is repeatedly subjected to an ion exchange process with aqueous 1N ammonium sulphate solution and subsequently mixed in a kneader in an amount of 70% aluminosilicate to 30% inorganic binder of aluminum oxide as psuedo-boehmite by weight of the mixture, with the addition of 3% by weight of concentrated nitric acid. The catalyst is then molded to extrudates of 3 mm diameter and activated at a temperature of 400° C.

Comparison Catalyst 2

A zeolite of type C, synthesized by the method of Jacobs, P. A. et al. (Example 10a on page 19 in "Synthesis of High-Silica Alumino-silicate Zeolites" in Stud. Surf. Sci. Catal., 33 (1987)) with tetrapropylammoniumbromide as structure-directing compound in accordance with Example 3. The zeolite is repeatedly subjected to an ion exchange process with an aqueous 1N ammonium sulphate solution and subsequently mixed in a kneader in an amount of 70% aluminosilicate to 30% inorganic binder of aluminum oxide as pseudo-boehmite by weight of the mixture, with addition of 3% by weight of concentrated $HNO_3$. The catalyst is then molded to extrudates of 3 mm diameter and activated at a temperature of 400° C.

Catalyst 3

A synthetic, crystalline aluminosilicate of type A, prepared in accordance to Example 1, is repeatedly subjected to an ion exchange process with aqueous ammonium sulphate solution and subsequently mixed in a kneader in an amount of 70% aluminosilicate to 30% inorganic binder (see catalyst 1) by weight of the mixture and molded to extrudates of 3 mm diameter. Subsequently, the molded catalyst is coated with 3% by weight of molybdenum oxide by impregnation with 1N ammonia molybdate and activated at a temperature of 400° C.

Comparison Catalyst 4

A zeolite of type C, synthesized by the method of Jacobs, P. A. et al. (Example 10a on page 19 in "Synthesis of High-Silica Alumino-silicate Zeolites" in Stud. Surf. Sci. Catal., 33 (1987)) with tetrapropylammonium bromide as structure-directing compound in accordance with Example 3. This zeolite is repeatedly subjected to an ion exchange process with an aqueous ammonium sulphate solution and subsequently mixed in a kneader in an amount of 70% aluminosilicate to 30% inorganic binder (see catalyst 1) by weight of the mixture and molded into extrudates with a diameter of 3 mm. The molded catalyst is subsequently coated with 3% by weight of molybdenum oxide by impregnation with 1N ammonia molybdate solution and activated at temperatures of 400° C.

Catalyst 5

A synthetic, crystalline aluminosilicate of type B prepared in accordance to Example 2 is repeatedly subjected to an ion exchange process with aqueous 1N ammonia sulphate solution and subsequently mixed in a kneader in an amount of 70% aluminosilicate to 30% inorganic binder (see catalyst 1) by weight of the mixture and molded to extrudates of 3 mm diameter. Subsequently, the molded catalyst is coated with 2% by weight of gallium oxide by impregnation with a gallium chloride solution in hydrochloric and activated at a temperature of 400° C.

Catalyst 6

A zeolite of type C is synthesized by the method of Jacobs, P. A. et al. (Example 10a on page 19 in "Synthesis of High-Silica Alumino-silicate Zeolites" in Stud. Surf. Sci. Catal., 33 (1987)) with tetrapropylammonium bromide as structure-directing compound as described in Example 3. This zeolite is repeatedly subjected to an ion exchange process with a 1N ammonium sulphate solution and subsequently mixed in a kneader in an amount of 70% aluminosilicate to 30% inorganic binder (see catalyst 1) by weight of the mixture, and molded to extrudates of 3 mm diameter. The catalyst is subsequently coated with 2% by weight of gallium oxide by impregnation with a gallium chloride solution in hydrochloric acid and activated at temperatures of 400° C.

Catalyst 7

A synthetic, crystalline aluminosilicate of type A prepared in accordance with Example 1 is repeatedly subjected to an ion exchange process with aqueous 1N ammonium sulphate solution and subsequently mixed in a kneader in an amount of 70% aluminosilicate to 30% inorganic binder (see catalyst 1) by weight of the mixture and molded to extrudates of 3 mm diameter. Subsequently, the molded catalyst is coated with 2% by weight of zinc nitrate by impregnation with a 1N zinc nitrate aqueous solution and activated in a current of hydrogen at a 40 bar $H_2$ pressure and a temperature of 400° C.

Comparison Catalyst 8

A zeolite of type C is synthesized by the method of Jacobs, P. A. et al. (Example 10a on page 19 in "Synthesis of High-Silica Alumino-silicate Zeolites" in *Stud. Surf. Sci. Catal.*, 33 (1987)) with tetrapropylammonium bromide as structure-directing compound as described in Example 3. This zeolite is repeatedly subjected to an ion exchange process with a 1N aqueous ammonium sulphate solution and subsequently mixed in a kneader in an amount of 70% aluminosilicate to 30% inorganic binder (see catalyst 1) by weight of the mixture, and molded to extrudates of 3 mm diameter. The catalyst is subsequently impregnated with a zinc nitrate (2% by weight) with 1N zinc nitrate aqueous solution and activated in a current of hydrogen at a 40 bar $H_2$ pressure and a temperature of 400° C.

EXAMPLE 5

Comparison of aluminosilicate catalysts in dewaxing hydrocarbon fractions

A gas oil (a crude oil distillate with a boiling point between about 290° C. and about 350° C.) with a density of 0.865 kg/L, a nitrogen content of 142 mg $NH_3$/L and a BPA point (temperature at which paraffin commences to precipitate) of 3° C. is reacted at a pressure of 3.5 MPa, a loading of 2 (v/v/hour) and a gas product ratio (GPV) of 1000:1 at an initial temperature of 663° K. on catalyst 7 and, in a separate run, on the conventional, comparison catalyst 8. The units (v/v/hour) refers to the volume of "liquid" educt, e.g. gas oil, divided by the volume of catalyst per hour. The results of the catalytic dewaxing are listed in the Table below:

The inventive catalyst 7 has a low fouling rate (T/day) and thus a higher stability with about the same initial activity as catalyst 8.

| Parameters | Starting Material | Catalyst 7 | Catalyst 8 |
|---|---|---|---|
| Density (kg/L) | 0.865 | 0.859 | 0.858 |
| BPA (°C.) | 3° C. | −15/−25 | −15/−25 |
| T/day (°K.) | | 0.17 | 0.48 |

T/day was determined over a period of 30 days and refers to the temperature (°K.) per day which has to be increased in order for the reaction to receive the same BPA point.

EXAMPLE 6

Comparison of Aluminosilicate catalysts in the isomerization of Xylene

A C-8 mixture of aromatic compounds is converted at a pressure of 1.0 MPa, a temperature of 400° C., a load of 2.0 (v/v/hour) and a gas product ratio (GPV) of 1000:1 on catalyst 3 and, in a separate run, on the conventional catalyst 4. The results of the conversion of the C-8 aromatic compounds are listed in the Table below.

| Compounds | Raw Material | Catalyst 3 | Catalyst 4 |
|---|---|---|---|
| Non-aromatics | 1.09 | 0.45 | 0.71 |
| Benzene | | 14.39 | 5.32 |
| Toluene | 0.71 | 6.62 | 5.04 |
| Ethylbenzene | 23.75 | 2.79 | 12.24 |
| para-xylene | 9.73 | 17.89 | 16.01 |
| meta-xylene | 47.57 | 40.38 | 38.12 |
| ortho-xylene | 16.44 | 16.29 | 15.27 |
| $C_9^+$ aromatics | 0.71 | 1.35 | 7.29 |
| Total xylenes | 73.74 | 74.5 | 69.4 |

Compared to the comparison catalyst 4, the inventive catalyst 3 exhibits a far higher ethylbenzene conversion and, at the same time, a better xylene selectivity (fewer aromatic materials).

EXAMPLE 7

Comparison of aluminosilicate catalysts in a process for alkylation of aromatic compounds A mixture of benzene and ethene, in a ratio of 1:2.6 gm/gm, is converted at 400° to 420° C. at a load of 6.5/hour (benzene plus ethene) over catalyst 1 and, in a separate run, over the conventional comparison catalyst 2.

Compared to the comparison catalyst 2, the inventive catalyst 1, has a slightly higher activity and selectivity for ethylbenzene and diethylbenzene and a distinctly better selectivity for para-diethylbenzene.

| Results | Catalyst 1 % Conversion | Catalyst 2 % Conversion |
|---|---|---|
| Conversion of benzene | 28 | 26 |
| Conversion of ethene | 81 | 72 |
| Selectivity of the benzene to ethylbenzene + diethylbenzene | 95 | 92 |
| Selectivity of the ethene to ethylbenzene + diethylbenzene | 90 | 90 |
| Proportion of para-diethyl-benzene in diethylbenezene | 85 | 60 |

EXAMPLE 8

Comparison of Aluminosilicate catalysts in a process for alkylation of toluene with methanol A mixture of toluene and methanol in the ratio of 2:1 is converted at a temperature of 350° C. and a loading of 4/hour (toluene plus methanol) over catalyst 1 and, in a different run, over the conventional comparison catalyst 2. The results of the alkylation reaction are listed in the Table below.

The inventive catalyst 1 shows a distinctly higher activity and a slightly better para selectivity than does the comparison catalyst 2.

| Results | Catalyst 1 % Conversion | Catalyst 2 % Conversion |
|---|---|---|
| Methanol conversion | 100 | 80 |
| Toluene conversion | 30 | 17 |

-continued

| Results | Catalyst 1 % Conversion | Catalyst 2 % Conversion |
|---|---|---|
| Benzene | 1 | 0.5 |
| Toluene | 51 | 61 |
| meta-Xylene | 8 | 4 |
| para-Xylene | 11 | 3.9 |
| ortho-Xylene | 7 | 3.0 |
| Total C8 aromatic compounds | 26 | 11 |

EXAMPLE 9

Comparison of Aluminosilicate catalysts in a process for cracking higher-boiling hydrocarbon fractions Catalyst 1 and catalyst 2 are each metered in as additive (5% by weight) to a conventional commercial fluidized bed catalyst or moving bed catalyst that is based on a Y zeolite. After a steam treatment of the catalysts at 750° C. for 17 hours, a hydrated gas oil is passed at a temperature of 475° C. and a load of 10/hour over the mixed catalyst. The results of the cracking experiments are listed in the Table below.

Compared to the comparison catalyst, the inventive catalyst brings about a slightly higher gas yield, a somewhat better gasoline yield and a distinctly lower proportion of coke. The isooctane portion increases greatly, so that the octane number is clearly improved. Likewise, the proportions of $C_3$ and $C_4$ olefins is increased; this is associated with an improvement in the research octane number.

| Results | Conventional Catalyst (% yield) | With 5% Catalyst 1 (% yield) | With 5% Catalyst 2 (% yield) |
|---|---|---|---|
| Methane | 0.5 | 0.5 | 0.5 |
| Ethane | 0.7 | 0.7 | 0.7 |
| Ethene | 0.6 | 0.5 | 0.5 |
| Propane | 3.3 | 4.7 | 3.5 |
| n-Butane | 2.7 | 2.9 | 2.8 |
| i-Butane | 2.0 | 1.9 | 1.9 |
| Total $C_4$ | 6.7 | 7.9 | 6.8 |
| $C_5 - C_2$ | 1.5 | 1.8 | 1.7 |
| (Gasoline) | 50.2 | 48.5 | 48.2 |
| Coke | 8.4 | 5.8 | 8.1 |

EXAMPLE 10

Comparison of aluminosilicate catalysts in a process for the isomerization of low molecular weight n-paraffins A 1:10 n-hexane/hydrogen mixture (gm/gm) is reacted at 300° C. and 4 MPa and a load of 1/hour on catalyst 7 and, in a separate run, on a conventional comparison catalyst 8 for comparison. The results of the reaction are listed in the Table below:

| Results | Catalyst 7 (% yield) | Catalyst 8 (% yield) |
|---|---|---|
| n-Hexane conversion | 48 | 25 |
| Hexane isomers/cracked prod. | 1.3 | 1.2 |

Compared to the conventional comparison catalyst, the inventive catalyst 7 shows a clearly higher activity and a slightly better hexane isomer/cracked products ratio.

EXAMPLE 11

Comparison of aluminosilicates in a process for preparing aromatic compounds from low molecular weight hydrocarbons n-Pentane is converted at a pressure of 0.1 MPa and a load of 1/hour at a temperature of 500° C. on catalyst 5 and, in a different run, on the conventional comparison catalyst 6. The results of the aromatization reaction are listed in the Table below.

| Results | Catalyst 1 (% yield) | Catalyst 2 (% yield) |
|---|---|---|
| Liquid product | 45 | 39.2 |
| Gases | 54.1 | 60.3 |
| Carbon | 0.9 | 0.5 |
| Aromatic products | 44.5 | 38.5 |

Compared to the conventional catalyst 6, the inventive catalyst 5 shows a better yield of aromatic compounds.

EXAMPLE 12

Comparison of aluminosilicate catalysts in a process for preparing liquid hydrocarbons and low molecular weight alkenes from methanol Methanol is converted at a pressure of 0.1 MPa, a temperature of 300° C. and a load of 1/hour on catalyst 1 and, in a different run, on the conventional comparison catalyst 2. The results of the reaction are listed in the Table below.

| Results | Catalyst 1 | Catalyst 2 |
|---|---|---|
| Conversion | 99% | 77% |
| Olefins | 33% | 23% |
| Aromatic materials | 12% | 15% |

Compared to conventional comparison catalysts, the inventive catalyst 1 shows a clearly higher activity and an improved olefin yield.

What is claimed is:

1. A process for the conversion of hydrocarbons into valuable intermediates comprising contacting said hydrocarbons with a catalyst comprising a synthetic crystalline aluminosilicate having the following chemical composition in terms of molar ratio:

(0–3)$M_2O:Al_2O_3$: (15–40) $SiO_2$: (0–40) $H_2O$ wherein M represents a metal cation, a proton, or an ammonium compound, said aluminosilicate having
 (I) a $SiO_2/Al_2O_3$ molar ratio at the surface of the crystalline structure that is equal to or greater than the $SiO_2/Al_2O_3$ molar ratio in the interior of the crystalline structure,
 (ii) said crystalline aluminosilicate has an X-ray diffraction diagram with X-ray reflections belonging to the following d values:

| d Values/Interplanar Spacing | Relative Intensity |
|---|---|
| 11.2 ± 0.3 | strong |
| 10.2 ± 0.3 | strong |
| 9.8 ± 0.2 | weak |
| 3.85 ± 0.1 | very strong |

-continued

| d Values/Interplanar Spacing | Relative Intensity |
|---|---|
| 3.83 ± 0.1 | strong |
| 3.75 ± 0.1 | strong |
| 3.73 ± 0.1 | strong |
| 3.60 ± 0.1 | weak |
| 3.06 ± 0.05 | weak |
| 3.00 ± 0.05 | weak |
| 2.01 ± 0.02 | weak |
| 1.99 ± 0.02 | weak. |

2. The process according to claim 1, wherein said aluminosilicate has a $^{29}$Si solid MAS nuclear magnetic resonance spectrum with absorption bands at about −100, −106, −112 and −116 ppm relative to the absorption band of a tetramethylsilane standard.

3. The process according to claim 1, wherein said conversion comprises removing n-paraffins or branched paraffins from hydrocarbon fractions by transforming said paraffins to form lower molecular weight hydrocarbons, at a pressure between about 1.0 and about 1.5 MPa and a temperature between about 250° C. and about 450° C.

4. The process according to claim 1, wherein said conversion comprises converting $C_8$ aromatic mixtures into ortho-xylene and paraxylene, at a pressure between about 0.5 and about 5.0 MPa and at a temperature between about 250° C. and about 500° C; wherein said $C_8$ aromatic mixture comprises ethyl benzene.

5. The process according to claim 1, wherein said conversion comprises alkylating aromatic compounds with low molecular weight alkenes to form an alkylated product, at a pressure between about 1.0 and about 5.0 MPa and at a temperature between about 350° C. and about 500° C.

6. The process according to claim 5, wherein said aromatic compound comprises benzene, said low molecular weight compound comprises ethene and said alkylated product comprises ethylbenzene.

7. The process according to claim 5 wherein said aromatic compound comprises benzene, said low molecular weight compound comprises propene and said alkylated product comprises cumene.

8. The process according to claim 1, wherein said conversion comprises alkylating aromatic compounds with low molecular weight alcohols, at a pressure between about 0.1 and about 0.5 MPa and at a temperature between about 250° C. and about 500° C.

9. The process according to claim 8, which comprises alkylating toluene with methanol to produce xylenes.

10. The process according to claim 1, wherein said conversion comprises cracking higher boiling hydrocarbon fractions on a fluidized or moving bed catalyst to form a lower boiling cracked product.

11. The process according to claim 1, wherein said conversion comprises isomerizing lower molecular weight n-paraffins to isoparaffins, at a pressure between about 0.5 and about 5 MPa and at a temperature between about 200° C. and about 500° C.

12. The process according to claim 1, wherein said conversion comprises preparing aromatic compounds from low molecular weight hydrocarbons, at a pressure between about 0.5 and about 5.0 MPa and at a temperature between about 500° C. and about 600° C.

13. The process according to claim 1, wherein said conversion comprises converting methanol to liquid hydrocarbons, low molecular weight alkanes, or alkenes, at a pressure between about 0.5 and about 5.0 MPa and at a temperature between about 250° C. and about 550° C.

14. The process according to claim 1, wherein said conversion comprises converting a mixture of benzene and ethene to ethylbenzene, at a temperature between about 400° C. and about 420° C. at a load of about 6.5 v/v/hr.

15. The process according to claim 14, wherein said mixture comprises benzene and ethene in a ratio of 1:2.6.

16. The process according to claim 1, wherein said conversion comprises dewaxing hydrocarbons, at a temperature between about 390° C. and about 450° C. at a load of about 2.0 v/v/hr.

17. The process according to claim 1, wherein said conversion comprises isomerizing xylene, at a temperature between about 350° C. and about 450° C. at a load of about 2.0 v/v/hr.

18. The process according to claim 1, wherein said conversion comprises alkylating toluene with methanol, wherein the mixture of toluene and methanol is at a ratio of about 2:1; at a temperature between about 300° C. and about 400° C., and at a load of about 4 v/v/hr.

19. The process according to claim 1, wherein said conversion comprises cracking hydrated gas oil, at a temperature between about 450° C. and about 500° C. at a load of about 10 v/v/hr.

20. The process according to claim 1, wherein said conversion comprises isomerizing low molecular weight n-paraffins, at a temperature between about 250° C. and about 350° C. at a load of about 1 v/v/hr.

21. The process according to claim 1, wherein said conversion comprises preparing aromatic compounds from low molecular weight hydrocarbons, at a temperature between about 500° C. and about 600° C. at a load of about 1 v/v/hr.

22. The process according to claim 1, wherein said conversion comprises preparing $C_4$ to $C_{12}$ liquid hydrocarbons and low molecular weight alkenes (<$C_6$) from methanol, at a temperature between about 250° C. and about 500° C. at a load of about 1 v/v/hr.

* * * * *